US010796390B2

(12) United States Patent
Kapit et al.

(10) Patent No.: US 10,796,390 B2
(45) Date of Patent: Oct. 6, 2020

(54) SYSTEM AND METHOD FOR MEDICAL CODING OF VASCULAR INTERVENTIONAL RADIOLOGY PROCEDURES

(75) Inventors: Andrew Kapit, Rockville, MD (US); Richard B. Toren, Washington, DC (US); Jean Stoner, Arlington, VA (US); Michael Niv, Dayton, MD (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 270 days.

(21) Appl. No.: 11/480,678

(22) Filed: Jul. 3, 2006

(65) Prior Publication Data

US 2008/0004505 A1   Jan. 3, 2008

(51) Int. Cl.
*G06Q 10/00* (2012.01)
*G06Q 50/00* (2012.01)
*G06Q 50/24* (2012.01)
*G16H 15/00* (2018.01)

(52) U.S. Cl.
CPC ............ *G06Q 50/24* (2013.01); *G16H 15/00* (2018.01)

(58) Field of Classification Search
CPC ........................... G06F 19/3487; G06Q 50/24
USPC ...................................................... 705/2, 3
See application file for complete search history.

(56) References Cited

U.S. PATENT DOCUMENTS

| | | | |
|---|---|---|---|
| 5,325,293 A * | 6/1994 | Dorne | 705/2 |
| 5,369,678 A * | 11/1994 | Chiu et al. | 378/62 |
| 5,483,443 A | 1/1996 | Milstein et al. | |
| 5,680,628 A | 10/1997 | Carus et al. | |
| 5,916,163 A * | 6/1999 | Panescu et al. | 600/424 |
| 6,055,494 A * | 4/2000 | Friedman | 704/9 |
| 6,182,029 B1 | 1/2001 | Friedman | |
| 6,246,901 B1 * | 6/2001 | Benaron | 600/431 |
| 6,292,767 B1 | 9/2001 | Jackson et al. | |
| 6,401,061 B1 | 6/2002 | Zieman | |
| 6,523,031 B1 | 2/2003 | Goeser | |
| 6,553,385 B2 | 4/2003 | Johnson et al. | |
| 6,684,276 B2 * | 1/2004 | Walker et al. | 710/73 |
| 6,695,861 B1 * | 2/2004 | Rosenberg et al. | 606/185 |
| 6,901,399 B1 | 5/2005 | Corston et al. | |
| 6,915,254 B1 * | 7/2005 | Heinze | G06F 17/27 704/9 |
| 6,925,433 B2 | 8/2005 | Stensmo | |
| 6,993,476 B1 | 1/2006 | Dutta et al. | |
| 7,136,806 B2 | 11/2006 | Miyahira et al. | |
| 7,136,807 B2 | 11/2006 | Mueller | |
| 7,191,119 B2 | 3/2007 | Epstein et al. | |
| 7,233,938 B2 * | 6/2007 | Carus et al. | 705/2 |
| 7,299,180 B2 | 11/2007 | Wang et al. | |
| 7,366,666 B2 | 4/2008 | Balchandran et al. | |

(Continued)

*Primary Examiner* — Trang T Nguyen
(74) *Attorney, Agent, or Firm* — Jonathan L. Tolstedt

(57) ABSTRACT

A system and method for identifying medical procedure codes and medical diagnosis codes from physician reports that describe a vascular interventional radiology procedure using a combination of natural language processing (NLP) and human medical coders. In one embodiment, the system and method of the present invention creates billing results, and or other documents, that are compliant with applicable legal and policy instructions from the government or a medical institution. Medical billing codes are efficiently extracted from medical reports using a NLP engine and a graphical user interface optimized for understanding the VasIR medical procedure described in the report.

27 Claims, 7 Drawing Sheets

(56) References Cited

U.S. PATENT DOCUMENTS

| | | |
|---|---|---|
| 7,493,253 B1 | 2/2009 | Ceusters et al. |
| 7,603,267 B2 | 10/2009 | Wang et al. |
| 7,684,975 B2 | 3/2010 | Aoki et al. |
| 7,707,027 B2 | 4/2010 | Balchandran et al. |
| 7,835,911 B2 | 11/2010 | Balchandran et al. |
| 7,953,754 B2 | 5/2011 | Cunnane et al. |
| 8,055,592 B2 | 11/2011 | Boyle et al. |
| 2003/0105638 A1* | 6/2003 | Taira .................... 704/275 |
| 2004/0073458 A1* | 4/2004 | Jensen ............... G06Q 10/10 705/2 |
| 2004/0243545 A1 | 12/2004 | Boone et al. |
| 2005/0108001 A1* | 5/2005 | Aarskog ............ G06F 17/271 704/10 |
| 2005/0149365 A1* | 7/2005 | Johnson ............ G06F 19/328 705/4 |
| 2005/0158767 A1* | 7/2005 | Haskell et al. .............. 435/6 |
| 2005/0228815 A1 | 10/2005 | Carus et al. |
| 2005/0240439 A1* | 10/2005 | Covit et al. ................ 705/2 |
| 2006/0020444 A1 | 1/2006 | Cousineau et al. |
| 2006/0020447 A1 | 1/2006 | Cousineau et al. |
| 2006/0020465 A1 | 1/2006 | Cousineau et al. |
| 2006/0020466 A1 | 1/2006 | Cousineau et al. |
| 2006/0020492 A1 | 1/2006 | Cousineau et al. |
| 2006/0020493 A1 | 1/2006 | Cousineau et al. |
| 2006/0149558 A1* | 7/2006 | Kahn et al. ............... 704/278 |
| 2007/0016614 A1* | 1/2007 | Novy ...................... 707/104.1 |
| 2007/0050187 A1* | 3/2007 | Cox .............................. 704/9 |
| 2007/0237378 A1* | 10/2007 | Reiner ............. G06F 3/04883 382/128 |
| 2010/0010805 A1 | 1/2010 | Balchandran et al. |
| 2010/0250236 A1 | 9/2010 | Jagannathan et al. |

* cited by examiner

Fig. 2

| | ICD Code | Description | | | | |
|---|---|---|---|---|---|---|
| I1 | 440.30 | Atherosclerosis of unspecified bypass graft of the extremities | | | | |
| I2 | 440.20 | Atherosclerosis of native arteries of the extremities, unspecified | | | | |
| I3 | 440.0 | Atherosclerosis of aorta | | | | |
| | | Add ICD Code | | | | |

APPROACH: FEMORAL

| | Side | Procedure / Vessel | Type | Filter | CPT Codes | ICD Codes |
|---|---|---|---|---|---|---|
| L1 | Right | Angioplasty Femoral | THER | None | 35474, 75962 | ☑ 440.30 ☑ 440.20 ☑ 440.0 |
| L2 | Bilat | Renal | S+I | Not selective | 75724 | |
| L3 | Right | External Iliac | S+I | None | 75774 | ☑ 440.30 ☑ 440.20 ☑ 440.0 |
| L4 | Unknown | Abdominal Aorta | S+I | None | 75625 | ☑ 440.30 ☑ 440.20 ☑ 440.0 |
| L5 | Right | Femoral | CATH | None | 36247 | ☑ 440.30 ☑ 440.20 ☑ 440.0 |
| L6 | Bilat | Common Iliac | S+I | None | 75716 | ☑ 440.30 ☑ 440.20 ☑ 440.0 |

Fig 5A and external iliac artery which is patent. There is
exte  CODING INFORMATION:
Approach: FEMORAL
Type: S+I
Side: Right
ss g  Procedure or Vessel:
f the
rem
Evidence: *external iliac artery*
Cancel   Add »

Fig 5B and external iliac artery which is patent. There is
exte  CODING INFORMATION:
Approach: FEMORAL
Type: S+I
Side: Right
ss g  Procedure or Vessel:
f the  ili
rem
Anterior Division Internal Iliac
Common Iliac
External Iliac
Iliolumbar
al byp  Internal Iliac                          m Bard
ass g  Posterior Division Internal Iliac      ellent
ypass  Trunk of Ascending Part of Deep
Circumflex Iliac
dure i  Umbilical                              as

SYSTEM AND METHOD FOR MEDICAL CODING OF VASCULAR INTERVENTIONAL RADIOLOGY PROCEDURES

BACKGROUND OF THE INVENTION

The invention relates to a method and a system for coding medical report documents and for optimizing accurate and compliant coding results, particularly in the field of vascular interventional radiology (VasIR).

In a general sense, interventional radiology concerns various imaging procedures that require some type of penetration of the body. The discipline may involve a combination of surgical procedures along with the supervision and interpretation of the results of the procedures. Typically, diagnostic radiology procedures are non-invasive, using various tools to image the body for diagnosis. However, in some cases, the radiologist will need to insert a medical device into the patient's body to facilitate the procedure. Usually, this is done for the purpose of delivering a tracer substance, for example, a dye or a contrast agent that helps create more detail in a medical image for a more complete, or more accurate diagnosis. There are a variety of procedures that fall into this category.

During various medical procedures, including VasIR procedures, a medical transcript is generated by one or more medical professionals. This transcription is typically lengthy, and has two primary components: (i) the medical procedure transcription describing the manipulation of the catheter through the body and the injection of dye, as done by the surgeon in the operating room; and (ii) a second transcription containing the supervision and interpretation (S&I) codes, which are a product of the review of the images obtained and the creation of a diagnosis as a result of this review.

In some cases a single physician performs the procedure as well as the S&I work, delivering to a medical report coder, such as CodeRyte™ one large transcription. In other cases, two different physicians provide a transcription, one for the procedure and one for the reading. Each of the catheter and the S&I procedures have a different code associated with it.

In VasIR procedures a small insertion is made to a vein or an artery, into which a very thin catheter is inserted. The radiologist pushes and directs the catheter through the circulatory system to inject a contrast agent at a specific location, or to use an imaging system to visually examine the inside of an artery. These procedures require special training and experience, and have a high financial value to the radiologist.

For billing and medical tracking purposes, billing codes are associated with various medical reports. While in some cases, the process of extracting medical codes from a medical report transcript is a simple one, in other cases, especially in VasIR procedures, abstraction of the medical codes is very difficult and time consuming to a medical coder. To effectively and efficiently generate medical codes relating to VasIR procedures, a human coder needs to have an understanding of vascular procedures, vascular anatomy, and the rules of vascular medical billing as defined by the American Medical Association, the Center for Medicaid and Medicare Services, as well as related rules from other commercial payers and state agencies. These rules are lengthy, complex, subject to change over time, and are subject to audit and review by the Office of Inspector General in the department of Health and Human Services. For example, Local Medical Review Policy (LMRP) is an administrative and educational tool to assist providers, physicians and suppliers in submitting correct claims for payment based on medical necessity. Local policies outline how contractors will review claims to ensure that they meet Medicare coverage requirements. Also, the Correct Coding Initiative (CCI) was created to promote correct coding methodologies and to control improper coding that leads to inappropriate payment of Part B health insurance claims.

From a financial point of view, it is important to associate the appropriate diagnosis code with a specific medical procedure, because financial compensation for the medical procedure will depend on the codes entered in the billing system. From a medical point of view, using the appropriate medical code will also facilitate the review and tracking of a patient's medical history.

The high cost and complexity of VasIR procedures combined with the complexity of the rules governing the coding of the procedures, create a likelihood of human error in the coding and a need for automating the coding of VasIR medical reports in order to efficiently provide consistent and compliant results.

Natural Language Processing, broadly speaking, is the technology of analyzing language through computer software to determine the structure of a document and the facts contained in it without the need for the document to be organized in a specific limited vocabulary. A 'natural language' is any of the languages naturally used by humans, i.e. not an artificial or man-made language such as a programming language. 'Natural Language Processing' (NLP) is a convenient description for all attempts to use computers to process natural language. The technology has been generally applied to language translation, voice-to-text applications, and population of databases with reduced need for human intervention. The use of NLP in the healthcare context has already been suggested. For example, U.S. Pat. No. 6,182,029 to Friedman teaches using a NLP system for extracting information from a natural language document, the system being adaptable to a medical, clinical or scientific application. However, the prior art in general, and Friedman in specific, have not addressed the need for automating the coding of VasIR medical reports.

SUMMARY OF THE INVENTION

To address the need for automating the coding of VasIR medical reports, in one embodiment of the present invention, medical billing codes are electronically assigned to medical reports using natural language processing (NLP) process. The results of the NLP process are then displayed on a custom graphical user interface (GUI) for review by human medical coders. Human coders review and approve the codes, and provide feedback to the NLP engine if corrections are needed. This feedback process provides training for the NLP engine, allowing it to add to its knowledge base over time and to expand its ability to provide reliable coding of VasIR medical reports.

The GUI interface may be customized and optimized to display, in detail, the medical report, important related data, and coding engine output relating to the vascular procedures. Human coders are then able to review the results, modify them, add to them and/or approve them through the GUI interface. In addition to providing the ability to review the medical report, the interface may list the facts identified by the NLP engine, and display a graphical vascular anatomy diagram that acts as a reference for reviewing and updating the billing codes. The GUI interface may also highlight the anatomical path of the VasIR procedure, providing a visual representation of any coding error caused by a break in the path. Such interface may advantageously assist a non-physician human coder in understanding the medical report. Additionally, the interface may also allow the coder to enter data using anatomical references without the need to memorize the billing codes, and may also calculate the codes appropriate for the anatomy and the billing rules. The custom GUI interface may facilitate significant savings in coding time, and may be utilized to facilitate more consistent and compliant coding results from the NLP engine and the human coder.

While the following disclosure focuses on coding VasIR procedures, the invention disclosed herein may be applicable and adaptable to various medical fields and clinical or scientific applications.

DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the figures, wherein:

FIG. 2 demonstrates an input table that allows human coders to make corrections to, and add, procedure codes.

FIG. 5(A) shows the portion of a user interface for adding a procedure or vessel.

FIG. 5(B) shows the portion of a user interface that displays a list of valid procedures and vessels in the database.

DETAILED DESCRIPTION OF THE INVENTION

One of the features of one embodiment of the present invention is a system and method for predicting medical diagnosis codes based on the metadata and language information present in a medical chart. Many computer systems can be viewed as making predictions based on a model. For example, speech recognition predicts what words were said based on the acoustic signal and the context, and fraud detection systems predict whether a transaction requires investigation based on features including the transaction type, amount, past history, etc. In one embodiment of the present invention, the prediction engine makes predictions (e.g. of procedure and diagnosis codes) for a chart based on the metadata and language information present in the chart.

Figure 1:
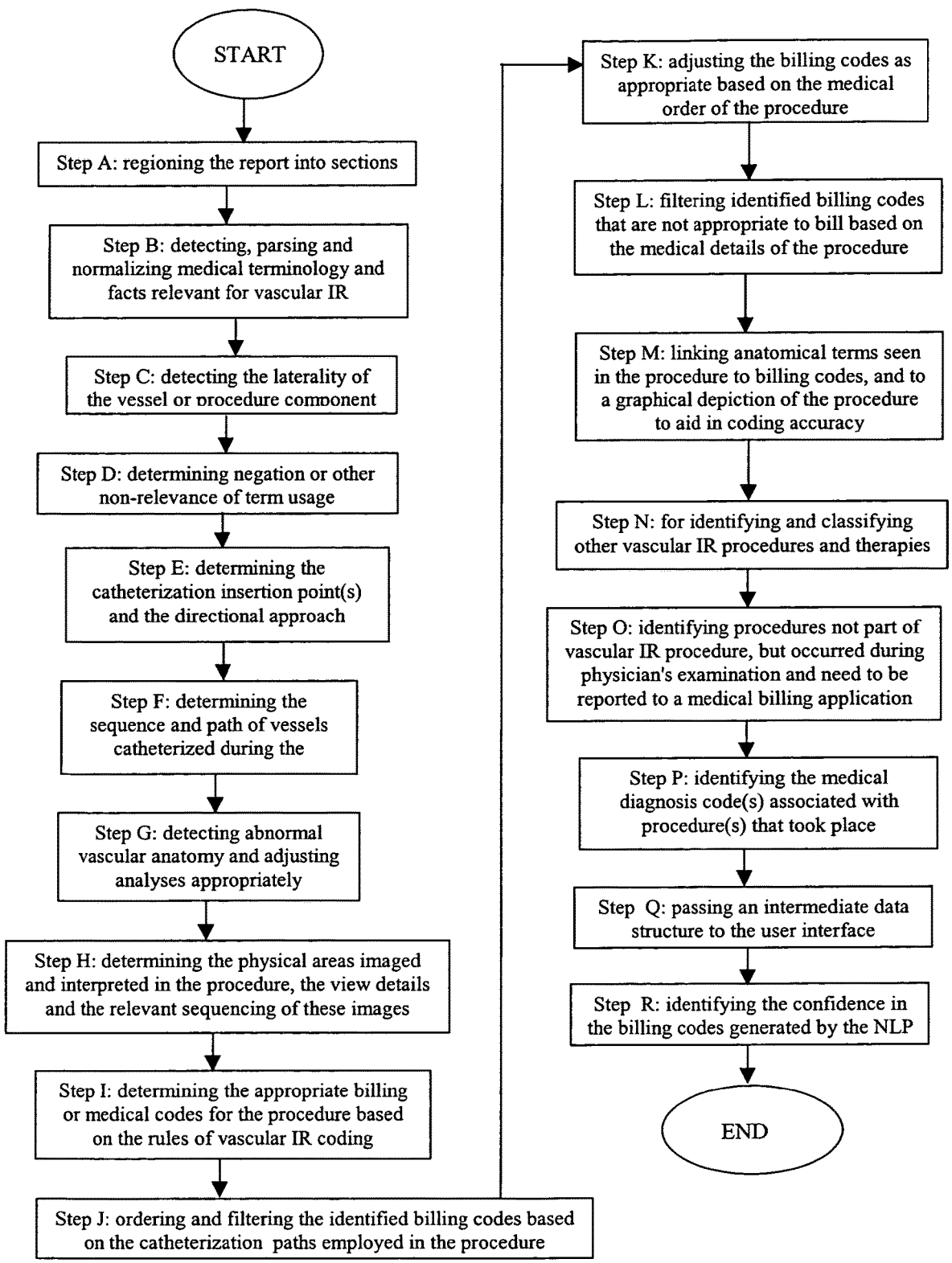
FIG. 1 is a flowchart of a process of extracting billing codes using natural language processing.

As shown in FIG. 1, according to one embodiment of the present invention, natural language processing (NLP) is used to extract billing codes by: (i) regioning the report into sections; (ii) detecting, parsing, and normalizing medical terminology and facts relevant to vascular IR; (iii) detecting the laterality of the vessel or procedure component; (iv) determining negation or other non-relevance of term usage; (v) determining the catheterization insertion point(s) and the directional approach; (vi) determining the sequence and path of vessels catheterized during the procedure; (vii) detecting abnormal vascular anatomy and adjusting the analysis appropriately; (viii) determining the physical areas imaged and interpreted in the procedure, the view details, and the relevant sequencing of these images; (ix) determining the appropriate billing or medical codes for the procedure based on the rules of vascular IR coding; (x) ordering and filtering the identified billing codes based on the catheterization paths employed in the procedure; (xi) adjusting the billing codes as appropriate based on the medical order of the procedure; (xii) filtering identified billing codes that are not appropriate to bill based on the medical details of the procedure; (xiii) linking anatomical terms seen in the procedure to billing codes, and to a graphical depiction of the procedure to aid in coding accuracy; (xiv) for identifying and classifying other vascular IR procedures and therapies; (xv) identifying procedures which may not be part of a vascular IR procedure, but which may have occurred during the physician's examination and which would need to be reported to a medical billing application; (xvi) identifying medical diagnosis code(s) associated with the procedure(s) that took place; (xvii) passing an intermediate data structure to the user interface identifying specific locations in the medical report where facts were located as offsets of text to drive text highlighting in the user interface; and (xviii) identifying the confidence in the billing codes generated by the NLP processing for the text examined, and reporting that confidence to the human coder.

Step A in FIG. 1 concerns regioning the report into sections. In order to interpret the medical language in a vascular IR report correctly, the major functional sections of the narrative that each sentence and phrase in the report corresponds to are determined. These functional sections or text regions typically include the following: (a) Catheterization description (CATH)—including the catheter insertion, vessel traversal and removal, with details of events and observations taking place in this process; (b) S&I imaging interpretation (S&I)—including medical analysis and interpretation of the radiological images obtained during the procedure; (c) Therapy description (THER)—including a description of therapies performed during the vascular IR procedure, for example, angioplasties (ANGP), embolizations (EMBOL), and the other major and minor types of therapies performed during vascular IR procedures; (d) Clinical indication or history (HIST)—including the presenting symptoms and preliminary diagnoses motivating the procedure; (e) Final Impression (IMPR)—including the final diagnostic impression of the patient's medical findings based on the results of the procedure(s); (f) Other dictation (OTHER)—including other dictated information not corresponding to the above functional sections; and (g) Non-dictated information (NONDICT)—including sections of the medical report not dictated by the physician, such as patient demographic information, transcription details, and physician practice details.

Each sentence within the report is assigned to one or more of the above functional regions, and for sentences containing multiple functional regions; each phrase (or subsequence of words) within the sentence is assigned to a single most-appropriate functional region. In each case, the approximate probability that the sentence/phrase belongs to the assigned functional region is also returned.

The regioning process consists of two phases: (1) a training phase, and (2) a runtime analysis phase. In the training phase, a set of medical reports with each sentence or phrase pre-annotated by functional region is statistically analyzed and the conditional probability P(region_i|phrase_j) and P(region_i|word_j) are computed for each observed phrase and word in the training data. Likewise, the transition probability of P(region_j|region_i) between adjacent sentences, phrases and words is computed by direct observation in the training data. At run time, the probability P(region_i|sentence_j) and P(region_i|phrase_j) for all region_i is computed via the training-time estimates of P(region_i|phrase_j), P(region_i|word_j) and P(region_j|region_i) using a Markov model. In parallel with the Markov models, regions containing strongly indicative phrases (where P(region_i|phrase_j) is high) are classified independently as region_i in cases where P(region_i|phrase_j) exceeds a threshold (tuned on held-out data) for one or more phrase_j in the sentence.

It will be understood that electronic data from the reports can be collected and fed into the coding system in a variety of ways, for example, through a network connection from the report originator to the coding entity. It should also be understood that information or data relating to a medical report or set of medical reports may be obtained from multiple data feeds and merged as desired to provide the coding entity with additional information concerning the patient, procedure or other related data.

Step B in FIG. 1 concerns detecting, parsing and normalizing medical terminology and facts relevant to vascular IR. The medical terminology relevant to vascular IR often occurs in multiple variant forms that need to be normalized and disambiguated. To accomplish this, a large database of vascular IR terms is created, particularly including all known human blood vessels (arteries and veins), such as the SUPERIOR_MESENTERIC_ARTERY. Second, a list of possible variant descriptions of terms, mapped to their standard term names (e.g. "SMA"=UPERIOR_MESENTERIC_ARTERY), is created. Described below is how this variant term list and the map to standardized forms are created and augmented semi-automatically from human coder feedback via the vascular IR workspace. An ensemble of regular expression recognition machines is then created for all standard and variant terms in this specialized database created for this purpose. At run time, all matching standard and variant forms of vascular IR terminology are located and annotated with the standard term name corresponding to each matched span of text. In the cases where there are multiple terms matching in a given span of text, a combination of longest string match, local word association and discourse state are used to prevent ambiguity. The primary use of "discourse state" is to disambiguate veins from arteries, a systematic ambiguity encountered when neither "artery" nor "vein" is explicitly stated for the vessel (by far the most common situation). Thus the term "the superior mesenteric" without explicit mention of artery or vein is resolved between SUPERIOR_MESENTERIC_ARTERY and SUPERIOR_MESENTERIC_VEIN by the discourse state feature of whether the arterial system or venous system is currently being traversed at the point of discussion. In the absence of disambiguating information, the standard term candidate with the highest Bayesian prior probability is preferred. The variant surface terminology patterns matched in the text need not be contiguous and may contain wildcards and structured subfields, such as number ranges, as part of the matching term pattern. The patterns may also be based on a morphological analysis of the term components to their uninflected lemma form. All relevant medical terminology, including basic procedure descriptions and components are handled in this common phrasal term matching and parsing framework.

Step C in FIG. 1 concerns detecting the laterality of the vessel or procedure component. In essentially all cases, the laterality (left, right, bilateral or none) of the dictated vessel or procedure component is a necessary distinction, yet the laterality information is often not stated explicitly or contiguously. A specialized analysis machine is created to determine the intended laterality of all salient vascular IR terminology, including vessels and procedure components. The laterality assignment of each such target term is based on the following features, in order of precedence: (1) an explicit and directly adjacent pre-modifying mention of laterality (e.g. "left common carotid"), (2) a direct but non-pre-modifying-contiguous syntactic relationship extracted by syntactic parsing (e.g. "the X on the left side"), (3) potentially ambiguous laterality description via pre-modifying conjunction (e.g. "the left common carotid and internal carotid"), (4) the consensus laterality of the current sentence (all laterality mentions agree) if at least one laterality mention is before the target term, (5) the nearest laterality term in the same sentence before the target term, (6) the consensus laterality of the current sentence if the only laterality mention follows the target term, (7) the nearest laterality term in the same sentence following the target term, (8) the consensus laterality in the preceding sentence (if all laterality terms in the previous sentence indicate the same laterality), (9) the latest mention of laterality in the preceding sentence if multiple literalities present, (10) the consensus laterality of the nearest preceding sentence containing a laterality term, and (11) other document-level laterality information.

Abbreviations and other variant laterality indicators are permitted and detected, including "right", "rgt", "rt", "r", etc., and disambiguated appropriately. A confidence score is associated with each laterality assignment based on the best present laterality feature in the precedence sequence above and the statistical likelihood of accuracy of each of these features (independently and in combination) based on their correlation with truth in laterality-annotated training data. Also, stand-alone laterality classification mechanisms have been developed and utilized for each of the above laterality features independently and in combination.

Step D in FIG. 1 concerns determining negation or other non-relevance of term usage. The determination of correct billing codes and other medical information extraction applications requires that linguistic evidence be identified (when present) indicating the negation/absence of some action or finding, or the other non-relevance of some action or finding. A mechanism is created to detect and exclude such contexts by using a set of both hand-crafted regular expression machines and syntactic phrasal contexts indicating negation/non-relevance, and statistical associations of such phrases and regular-expression-machine matches with negation/non-relevance as statistically observed with confidence in an annotated training data set. Negated/non-relevant phrasal contexts are identified and demarcated using the longest-matching expressions in this terminological inventory specialized and crafted for this purpose, and/or the highest confidence matching expressions. Types of negated/non-relevant context detectors that have been instantiated by this general mechanism include, but are not limited to, detectors of actions/findings that are either: (1) explicitly not done/not found, (2) done at a future time, (3) done (or observed) at a time previous to the dictated encounter, (4) started but not completed during the dictated encounter do to some interrupting factor, (5) only contemplated but not yet performed, (6) only recommended but not yet performed, (7) ordered but not yet performed, (8) findings to be ruled out, (9) actions/findings relevant to individuals other than the patient. An ensemble of one or more of all of these separate detection mechanisms is applied to the data and the marked contexts are excluded from subsequent extraction of actions or findings.

Step E in FIG. 1 concerns determining the catheterization insertion point(s) and the directional approach. The determination of correct billing codes and other medical information extraction applications requires the determination of the catheterization insertion point(s) and the directional approach (e.g. retrograde). A specialized mechanism is developed to detect catheter insertion points and approach directions utilizing (1) a set of hand-crafted regular expression machines of confident phrasal descriptions of insertion point and approach (e.g. "the right groin area was prepped and . . . was inserted into the femoral artery"), and (2) a database of partial phrasal descriptions of insertion point and approach information and correlation statistics between these features and the true insertion point in annotated training data, utilized in a standard Bayesian classification framework. In the absence of explicit information about insertion point and directional approach, the "standard approach" for the procedure in question is utilized as the default.

Step F in FIG. 1 concerns determining the sequence and path of vessels catheterized during the procedure. The determination of correct billing codes and other medical information extraction applications requires the determination of the sequence and path of vessels catheterized during the vascular IR procedure. To accomplish this, a database is created of vessel branching topology for the entire human arterial and venous system (e.g. RIGHT_EXTERNAL_CAROTID arises from RIGHT_COMMON_CAROTID). Utilizing these anatomical constraints, the sequence of vessels catheterized is determined by first extracting those vessels detected in step (B) and also appearing in a text region labeled in step (A) as CATH (catheterization descriptions) and not excluded by the negation/non-relevance detection module in step (D). The relevant laterality of each detected vessel is also incorporated from step (C). The resulting laterealized and filtered vessel lists are then sequenced by a mechanism incorporating (1) the order in which these catheterization region (CATH) descriptions of vessels were dictated in the report; (2) regular expression machines that match linguistic terms and syntactic patterns indicating temporal or physical catheterization sequence (e.g. "after X, Y was performed"); and (3) the anatomical constraints described above (catheterization of the RIGHT_EXTERNAL_CAROTID must first traverse the RIGHT_COMMON_CAROTID). The location/sequence of any therapies (such as angioplasties) are equivalently contextualized and sequenced using the same mechanism.

Step G in FIG. 1 concerns detecting abnormal vascular anatomy and adjusting the analysis appropriately. The determination of correct billing codes and other medical information extraction applications requires that abnormal vascular anatomy be detected and applicable analysis be adjusted accordingly. The classic (and relatively common) instance of abnormal vascular anatomy is the "bovine arch", where the left common carotid artery branches from the brachiocephalic artery rather than directly from the aorta, effecting the number of branches traversed in the catheterization process and hence the corresponding complexity code. Specialized regular expression machines are created to detect the numerous variant ways of referring to this anatomical abnormality (e.g. "the arch was bovined") and the anatomical attachment tables utilized in mechanism (F) are adjusted accordingly. For the purposes of data representation, LEFT_INTERNAL_CAROTID # BOVINE is treated as a distinct vessel with its own appropriate vascular branching and attachment topology in step (F). Other anatomical abnormalities in vascular attachment are detected and handled via the same mechanism.

Step H in FIG. 1 concerns determining the physical areas imaged and interpreted in the procedure, the view details and the relevant sequencing of these images. The determination of correct billing codes and other medical information extraction applications requires the detection and classification of physical areas imaged and interpreted in the procedure, the view details and the relevant sequencing of these images. A mechanism was created to accomplish this using a mechanism analogous to that used for tracing the catheterization of vascular structures. Those vessels detected in step (B) and discussed in a region labeled as S&I in step (A) and not excluded by the negation/non-relevance detection module in step (D) are considered. The relevant laterality of each detected vessel is also incorporated from step (C). Relevant view details and sequencing information are also extracted using a mechanism based on step (F). The resulting latereralized and filtered vessel lists are then further condensed by merging those vessels independently detected in S&I sections with both left and right laterality by a joint BILATERAL entry for the vessel. Furthermore, general region features such as BILATERAL_LOWER_EXTREMITIES are then activated by an association table of vessel membership by area. This candidate set of imaged and interpreted vessels are entered into the vascular IR workspace for subsequent coding and/or information extraction.

Step I in FIG. 1 concerns determining the appropriate billing codes for the procedure based on the rules of vascular IR coding. Once step (F) has determined the sequence of lateralized vessels that have been catheterized in the procedure, and the insertion point/approach (e.g. RIGHT_FEMORAL) has been detected in step (E), the corresponding candidate procedure code is determined by looking up the tuple of <vessel,laterality,approach>=code in a pre-computed table. Likewise, the S&I imaging codes are determined by looking up the <vessel,laterality> tuples and <vessel_region,laterality> tuples in an equivalent table. S&I coding is generally independent of the catheterization approach.

Step J in FIG. 1 concerns ordering and filtering the identified billing codes based on the catheterization paths employed in the procedure. Medical procedure coding rules require that certain vessels not be coded if they are on the catheterization pathway of more distant vessels that are also coded. Based on the vessel catheterization sequence determined in step (F), and an ON_PATH(vessel1, vessle2) table, those intermediate vessel catheterization descriptions not allowed to be coded under medical rules are marked with an ON_PATH filter code in the vascular IR workspace.

Step K in FIG. 1 concerns adjusting the billing codes as appropriate based on the medical order of the procedure. Likewise, when multiple most-distant vessels (not filtered in step J) are catheterized in the same vascular "family" (i.e. sharing the same branch from the aorta or vena cava), the billing codes for catheterization occurrences of additional vessels in the same family are assigned a different billing code. To determine the circumstances in which this adjustment should occur, a function FAMILY(vessel, laterality) is computed and when FAMILY(vessel_i, laterality_i)=FAMILY(vessel_j, laterality_j) for some previously coded vessel_i, the billing code for vessel_j is adjusted as per medical coding rules. Similar applications of code transformations based on other detailed medical coding rules are employed as appropriate.

Step L in FIG. 1 concerns filtering identified billing codes that are not appropriate to bill based on the medical details of the procedure. Medical coding rules also require that certain S&I imaging and interpretation codes only be coded when the vessel(s) in question have been selectively catheterized (i.e. the catheter inserted directly into the vessel as opposed to having dye injected into the vessel from a distance without direct catheterization). The candidate S&I codes determined in step (H) are compared with those selectively catheterized as detected in step (F) and those matching S&I entries are marked in the workspace being selectively catheterized. A regular-expression detection of an explicit linguistic description of selective catheterization of the vessel is also used to mark selective catheterization in the workspace. Those S&I codes appearing in a table requiring selective catheterization and not marked in the workspace as being selectively catheterized are filtered with a not-selectivily-catherized-when-required annotation and these codes are not generated for billing purposes. Similar applications of detailed medical logic rules are utilized to filter inappropriate billing codes as appropriate.

Step M in FIG. 1 concerns linking anatomical terms seen in the procedure to billing codes, and to a graphical depiction of the procedure to aid in coding accuracy. At all steps (A) through (L) where textual patterns are detected, the starting and ending character offsets of the matching text are recorded along with their associated workspace entry. Thus any generated billing code in the workspace is associated with both the normalized vessel name, laterality, etc. motivating the code and a highlightable pointer to the start/ending position of the original motivating text. Likewise, the associated normalized vessel name and laterality stored in the workspace are also linked directly to anatomical regions in the GUI, allowing for the highlighting of the catheterized and imaged vessels as desired, as described below.

Step N in FIG. 1 concerns identifying and classifying other vascular IR procedures and therapies. Other vascular IR procedures such as angioplasties and embolizations are handled using essentially the same sequence of mechanisms (A) through (M) as used for the default angiogram application described above. The major difference is that if the ANGP or EMBOL or other THER description regions are detected in step (A), the detected vessels and other vascular-IR-relevant information identified in step (B) is looked up in a table of angioplasties and embolizations, etc. for mapping to the candidate procedure codes in step (I) above. Another difference is that depending on the other therapy type, additional features (such as use of coil, etc.) are added to the code lookup hash table, equivalent to the addition of the laterality feature to the vessel in step (I). The treatment of the S&I codes is essentially the same as described above, although the candidate set of acceptable matching S&I codes for these additional therapies is often significantly more constrained than in the default angiogram case, and serve as a default S&I code in the case of ambiguity.

Step O in FIG. 1 concerns identifying procedures which may not be part of a vascular IR procedure, but which may have occurred during the physician's examination and which would need to be reported to a medical billing application. Additional non-vascular IR procedures are handled in one of two ways. Additional procedures commonly found in vascular IR notes, such as conscious sedation, are treated in the same mechanism as described in section (N). Alternately, non-vascular IR procedures can be passed through to a high-coverage diagnostic radiology engine for analysis.

Step P in FIG. 1 concerns identifying medical diagnosis codes (ICD-9) associated with the procedures that took place. "Parsing" of medical facts in the chart leads to the creation of a set of features associated with each identified piece of diagnosis evidence; we can represent this information as a feature vector Fi associated with an ICD code i. For example, given a chunk of text evidence e such as like "history of left sided pains in the abdomen", Fi might specify
t=HISTORY ("type", e.g. history, followup, rule-out, etc.)
m=LEFT_SIDED ("modifier" of bodypart) h=ABDOMEN (linguistic "head" of bodypart) w=PAIN ("what", i.e. symptom or diagnosis) reg=CLIN_HIST (chart region where this evidence was found) rule=R123 (rule used to assign code i based on this evidence), etc.

Note that feature values are not, strictly, words, even though they often look like words. Above we use uppercase to make the distinction clear—for example, PAIN is a more general feature value that can result from multiple alternative linguistic expressions (e.g. both "pain" and "pains"). The confidence associated with an ICD code is an estimate of Pr(icd=i|Fi); that is, the conditional probability that, given this combination of features, the ICD code associated with this evidence is 'i.'

The "ICD training" process analyzes charts that have been automatically coded and reviewed by human coders in order to identify combinations (i,e,Fi), where i is the ICD code assigned by the human coder, e is a piece of language evidence, and Fi is vector of features resulting from NLP analysis. Since the human coders typically do not identify e explicitly (they add, delete, or change codes without pointing out where the evidence came from), obtaining the frequencies needed to estimate Pr(icd=i|Fi) requires an alignment process that takes explicit advantage of the fact that human coders in the workflow are interacting with the chart. One can view the set of coder actions as producing a set of events <action,i',(i,e,Fi)> where i' is the post-review code and action is what the human coder did to get it there. These include: <CONFIRM, i, (i,e,Fi)> <DELETE, NULL, (i,e, Fi)> <CHANGE, i', (i,e,Fi)> <ADD, i', NULL>.

Analysis of these tuples leads to a table of raw frequencies; e.g. a CONFIRM for i,Fi leads us to increment the frequency of (i,Fi). These raw frequencies are converted to conditional probabilities Pr(i|fi) using standard probability estimation techniques.

Step Q of FIG. 1 concerns passing an intermediate data structure to the user interface identifying specific locations in the medical report where facts were located as offsets of text to drive text highlighting in the user interface.

Step R in FIG. 1 concerns identifying the confidence in the billing codes generated by the NLP processing for the text examined, and reporting that confidence to the human coder.

As mentioned earlier, the prediction engine of the present invention makes predictions (e.g. of procedure and diagnosis codes) for a chart based on the metadata and language information present in the chart. In many predictive settings, the computational system not only makes its best prediction, but also reports or adjusts its behavior based on the extent to which its prediction can be considered reliable. This is a different problem from the prediction itself. Prediction can be viewed as seeking the choice C such that Pr(choice=C|evidence) is maximized, i.e. the best choice among alternatives given the evidence, whereas the reliability of a prediction abstractly concerns the probability Pr(choice C is correct|evidence), i.e. the probability that the yes-or-no answer to "Is C the right choice?" is yes. Methods for assessing that probability can be grouped together as "confidence assessment" techniques and they play a role in many predictive settings.

One of the features of a preferred embodiment of the present invention, is a novel approach to confidence assessment that embeds the confidence assessment within a human-in-the-loop workflow that specifically involves human approval or lack of approval. In other words, a preferred aspect of the present invention assesses specifically the likelihood that a human coder will push the "approve" button in response to the engine's coding. This advantageously provides integration with an ongoing production process, versus confidence assessment techniques that use a (typically static) "gold standard" for correctness, i.e. a set of data held out from predictive-model estimation that is used to create a confidence model.

Another preferred feature of one embodiment of the present invention, is a system and method for combining code-level confidence assessments, in order to make a chart-level assessment. Yet another preferred feature of the present invention, is using the above-mentioned chart-level confidence to route notes to different queues in order to optimize the human coder's experience, and optimize efficiency gains in the computer-assisted coding process.

The engine produces CPT (procedure) and ICD (diagnosis) codes, and every ICD code is linked to a single CPT code. (Often a single CPT code will have multiple ICD codes associated with it, but not vice versa.) We can therefore view the engine's predicted codes as defining a set of vectors (c,i,Fc,Fi,V), where c is the CPT code, i is the ICD code, Fc is a vector of evidence used in selecting the CPT code (i.e. maximizing Pr(c|Fc)), Fi is a vector of evidence used in selecting the ICD code (i.e. maximizing Pr(i|Fi)), and V is a vector of other information available in (or created for) the chart of the particular (i,c) pair. A preferred confidence assessment technique involves the following steps: 1. Training; 2. Runtime code-level confidence assessment; 3. Runtime chart-level confidence assessment; and 4. Confidence-based routing to queues.

The workflow of one embodiment of the presently preferred invention includes human coders who review notes and either approve them without changes, or modify the codes. Human action may also cause dictation to modified by the physician when the coder identifies bad language they can ask the physician for an addendum to clarify their document. It will be understood that human coders can be located locally or remotely from the coding entity. The use of coder feedback from within the workflow is one of the advantages of the presently preferred invention. In the case where a human coder approves the notes, approval that every reported vector (c,i,Fc,Fi,V) involves a correct code pair (c,i), and therefore that approval action can be viewed as producing a "labeled" pair <(c,i,Fc,Fi,V),1>, where a label of 1 indicates "correct". Conversely, if the note was not approved without modification, then—regardless of the specific changes, the action can be viewed as producing a "labeled" pair <(c,i,Fc,Fi,V),0>, where a label of 0 indicates "incorrect". Given a data set containing <(c,i,Fc,Fi,V),label> items, a binary classifier is trained. Any supervised binary classification technique can be used—e.g. decision trees, support vector machines, etc.

The separation in the workspace between medical facts and codes determined based on those facts, may be used to differentially collect feedback from user-corrections in the GUI about the medical-fact-extractor and the fact-to-code mapper. These two feedback data streams may be used to separately train and/or refine two sub-systems: (1) the medical-fact-extractor; and (2) the fact-to-code mapper. This separation of users' feedback facilitates identifying the component system that requires change, and how it is to be changed.

When a user makes changes to the engine derived codes, these changes are passed back through the engine logic for VasIR coding through a recalculating ("recalc") process. This feature allows reusing the engine VasIR coding rules to verify that the human coder's rules are in the proper order.

Furthermore, the learning process feeds back user corrections to the engine in a very granular way, specifically adjusting how documents are parsed for medical facts, as well as adjusting the specific code mapping that is part of VasIR billing rules.

In one embodiment of the present invention, a decision tree classifier is built. Each individual data feed has its own classifier, so that confidence assessment comprises modeling the specific approval decisions associated with that customer and site. There are a large number of features in Fc, Fi, and V. Examples include linguistic features in the chart evidence. For example, one feature indicates that the diagnosis term evidence was headed by the term "fracture"; another, engine-determine feature, reflects that an ICD for "ankle fracture" superseded by another diagnosis, such as "ankle pain", in the logic for most-certain coding.

The binary classifier computes a confidence in the range $[0,1]$ for each input $<(c,i,Fc,Fi,V)>$ corresponding to reported CPT and ICD codes of c and i, respectively. This can be interpreted as $Pr(label=1|<(c,i,Fc,Fi,V))$, i.e., the probability that this CPT and ICD combination is correct.

In order to combine evidence about multiple code reports (c,i), the minimum value is taken over $Pr(label=1|<(c,i,Fc,Fi,V))$ as the confidence value for the entire chart. Since compliance is an important focus of the present invention, a conservative strategy is employed by considering the entire set of codes for a chart only as strong as the weakest link. In one embodiment of the present invention, every code reported in the chart must pass a confidence threshold in order for the whole chart to pass that threshold.

The confidence assessment score has an intuitively clear interpretation. It is not just a heuristic value; rather, it can be viewed as a conservative estimate (because of the "weakest link" property) that a human coder (in the specific workflow associated with this customer site) would accept the entire chart as correct without making any changes.

Another embodiment of the present invention uses the confidence assessment values to determine whether or not a chart is considered correct as coded (and therefore appropriate for the "Confident" queue), or whether there is some element (c,i) that fails to meet the confidence threshold and requires human review (in which case the chart belongs in the "Review" queue). The confidence threshold may be set manually in concert with the customer. Typical threshold values (>95%) are much higher than typical levels of inter-coder agreement even between experienced human coders.

In addition to the modeling described above, the presently preferred invention may also use a rule-based approach to determine whether a chart should be treated as a note to be coded from scratch—e.g., if a crucial region like the impressions section is missing, or if the engine detected procedure or diagnosis evidence that it deemed not codable. These rules will route notes to the "Code" queue rather than the "Review" queue. However, it should be noted that many notes in the "Code" queue do not wind up requiring coding from scratch: often the engine may have found and reported correct codes that are kept on review by the human coder, even though the rules have caught a serious issue that causes the engine to flag the entire chart as one that needs careful human attention. This underscores the focus on conservative approaches to ensure compliance.

Another feature of one embodiment of the present invention, is providing a mechanism for outputting the resulting codes from the NLP process to a GUI user interface optimized for a human coder to review the results and make changes as appropriate. The NLP-based coding engine does not always produce perfect results. However, the accuracy and consistency of the results may be greatly improved through the correction of the results by human coders. The interaction between the NLP-based engine and human coders is an activity in which the person and the machine collaborate on achieving a correct coding outcome. In one embodiment of the present invention, this interaction takes place through a custom GUI interface designed to display textual and graphical information that can be approved or disapproved by a human coder. The end result of that collaboration may be used for training the engine to consistently produce more accurate results.

The NLP-based coding engine can be broken out into two components, each with separate characteristics: (1) NLP concept and context extractor: scan text, identify medical facts; and (2) fact-to-code mapper (in the case of VasIR its blood vessels, laterality, procedures, entry points, i.e. "approaches"). In the case of VasIR it is an algorithmic mapping from fact extracted from component (1) to CPT codes. Component (2) is built in a way that completely covers all the logic for a particular medical coding domain (eg. vascular IR, or Evaluation and Management).

FIG. 2 shows how for each ICD code 10 found by the NLP engine, both the code and the description 11 may be displayed for the user. Procedure codes may be presented in order of "type" (e.g., surgical, S&I, non-billed) and in order of relative value unit largest to smallest. Coders may enter additional ICD codes in input box 13. When they click the "Add ICD Code" button 14, the description for the code added is pulled from the database. ICD codes are associated with CPT codes by checking check boxes 15 that precede the ICD code on right-most column in the CPT table. The approach 16 for the procedure is displayed above the CPT table. Engine supplied CPT codes can be changed by the user by double-clicking on the CPT code. A warning message, however, (not shown in FIG. 2) may be displayed to indicate the override will circumvent the engine before the user is allowed to edit the code. Preferably, once the coder has accepted the warning message, the coder is not interrupted again for other changes.

Figures 3, 4:
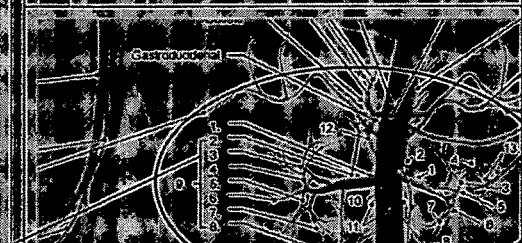
FIG. 3 shows an interface for checking the validity of the codes entered.
FIG. 4 demonstrates the highlighting mechanism of the interface.

FIG. 3 shows an interface for checking the validity of the codes entered. An error message 20 is displaced in the event of a conflicts between the NLP engine's result and the human coder's result. The interface has built in validations to prevent a coder from approving a report that is either incomplete, or that violates certain or all coding rules. Row L2 in FIG. 3 shows how errors and warnings are highlighted to the user. Validity messages may include a visual indication 21 in the form of an icon (red X for errors, yellow ! for warnings), the row identifier in either the ICD or CPT table, and a detailed description of the issue the coder must resolve, or at least be aware of. The primacy validation ensures the ICD code in the primary location is correct for all procedures.

FIG. 4 demonstrates a highlighting feature of the interface. This mechanism shows the specific text 30 that identifies the procedure code in the report by highlighting it and automatically scrolling the report to the exact location of the text or user review. To assist the coder in quickly visualizing the language in the report that the NLP engine identified for each procedure, when a user clicks on a row (for example, row L2 in FIG. 4) in the procedure table, the text in the report is highlighted. If the highlighted text is not visible in the report window, the interface may automatically adjust the window to display the highlighted text. Similarly, as shown in FIG. 4, vessels 31 in the graphic are highlighted and the view is centered on the highlighted vessel(s). Preferably, the interface also provides an integrated encoder function that allows the user to reference medical codes and their meaning. It should also be noted that the coloring chosen for highlighting are ADA compliant, allowing visually impaired individuals to understand displayed information.

Another preferred feature of the present invention, is a mechanism for the NLP engine and Coding-Workspace based GUI to interact. When a medical report is processed by the system, the NLP engine runs in its entirety (see FIG. 1). This includes the medical fact extractor (steps A through H) and the subsequent fact-to-code mapper (steps I through L). The engine-extracted medical facts are presented in the graphical user interface (GUI) in the left-side of the coding workspace, and the corresponding codes are presented on the right side. The graphical interface allows zooming, panning, and side views of the images. The user can then change, add, or remove medical facts. The user can click a recalculate button that runs the latest set of medical facts through the fact-to-code component of the NLP engine, and updates the codes. The process of changing medical facts and recalculating can then be repeated.

Yet another preferred feature of the present invention, is a learning feedback loop that allows changes made by the human coder to be identified specifically and sent back to the NLP engine. A human coder using a mouse can select text missed by the engine, identify the anatomy feature in the vascular path, and paste the resulting procedure code into the medical billing results. The text, location, and procedure code are sent back to the NLP engine server to allow the missed language to be learned by the technology and appropriate adjustments made to the engine.

To add a procedure or vessel in the VasIR interface, the coder must provide text evidence and provide the type of procedure, side, and select a valid vessel or procedure. FIG. 5A shows the dialog 40 that appears after the language evidence is highlighted within the report.

Figure 5C:
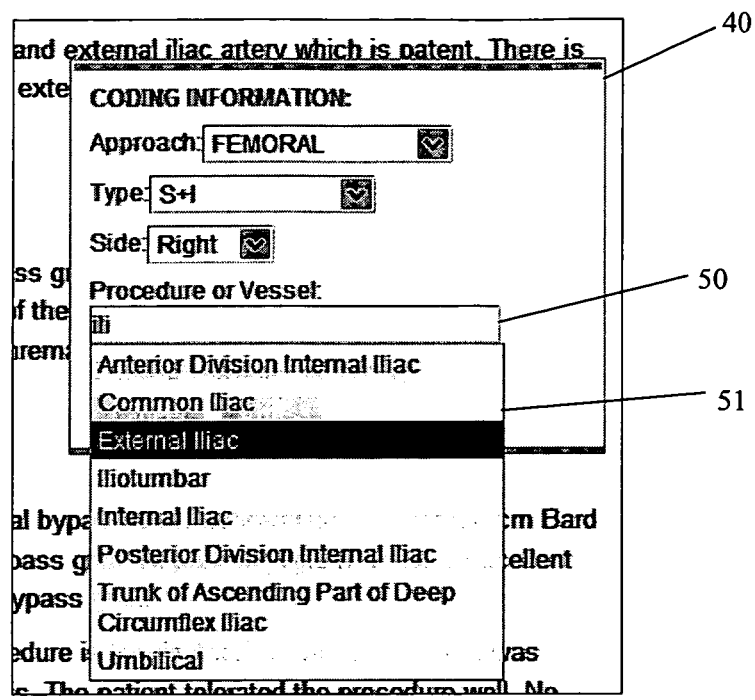
FIG. 5(C) shows the portion of a user interface that chooses and highlights a valid procedures and vessels in the database according to text entered by the user.

As demonstrated in FIGS. 5B and 5C, to assist the coder in finding the correct vessel or procedure, as the coder types in the Procedure or Vessel name in input field 50, a valid list of selection 51 is displayed that matches what the user has typed. This is an active search against the database of valid procedures and vessels, thus as the user continues to type in input field 50, the list of possible matches is reduced until the user selects the correct value by highlighting it in the list of selection 51 and clicking the mouse button. FIGS. 5B and 5C show an example of a user typing "Illiac" to find the "External Illiac," which matches the highlighted text evidence.

Figure 6A:
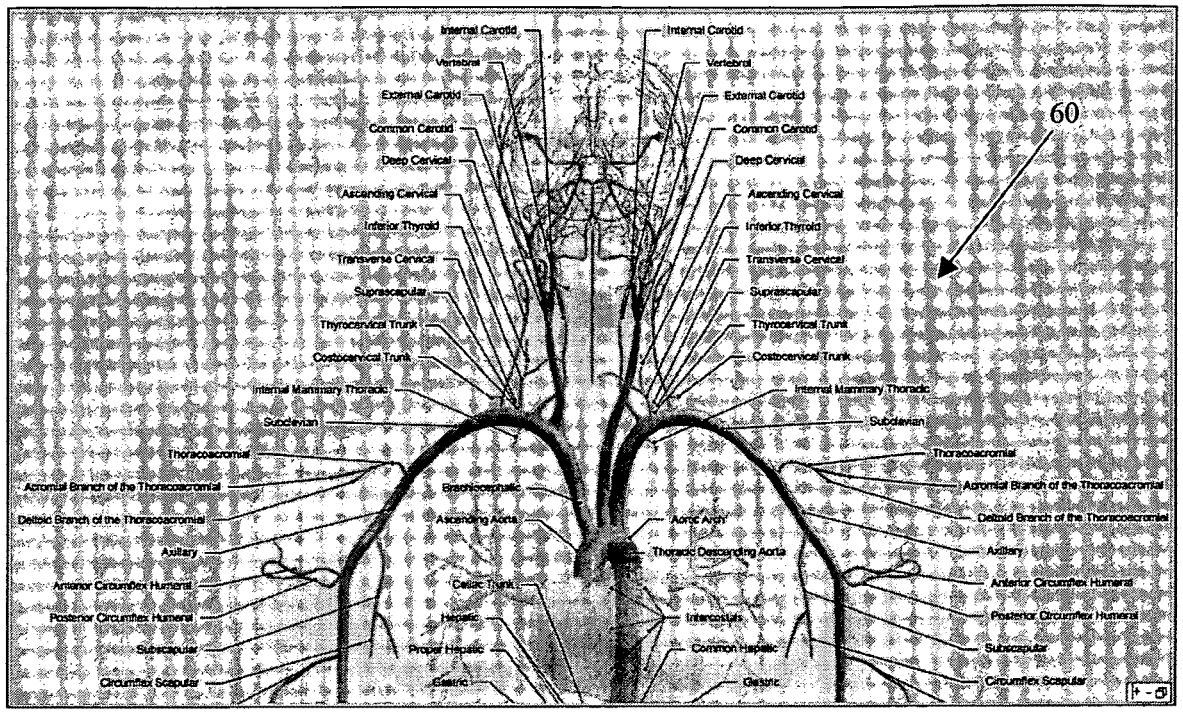
FIG. 6(A) shows a vascular diagram with vessel labels that adjusts appropriately to the gender of the patient.
Figure 6B:
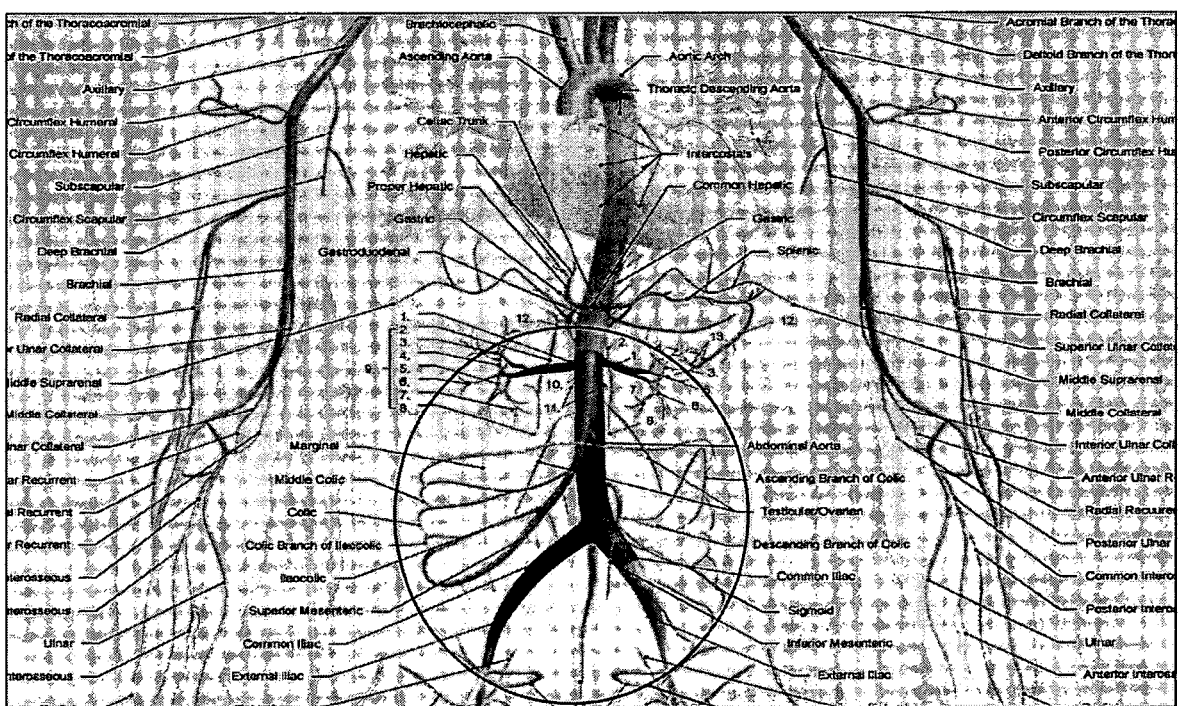
FIG. 6(B) shows a vascular diagram with vessel highlighting based on catheter placement.
Figure 6C:
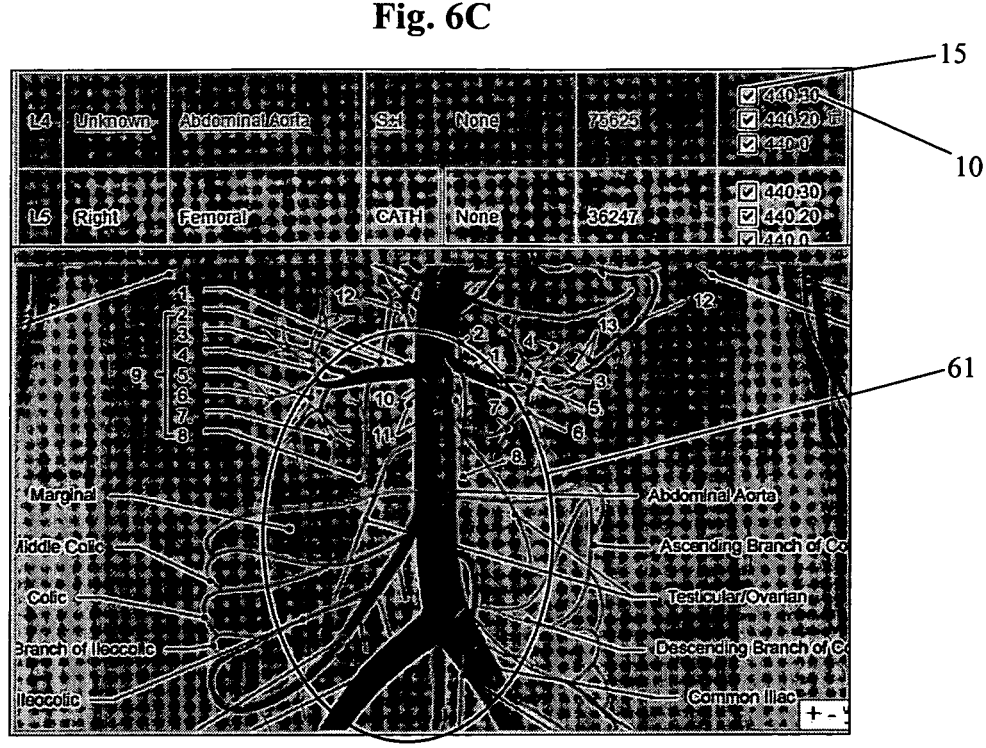
FIG. 6(C) shows a vascular diagram with vessel highlighting when a 'procedure row' option is selected.

As shown in FIGS. 6A, 6B and 6C, a graphical anatomy reference tool displays the vascular anatomy to the human coder, providing a reference to the human coder consisting of a complete vascular diagram of a patient. Vascular diagram 60 adjusts appropriately to the gender of the patient (there are anatomical differences between genders in the vasculature) as well as common aortic anomalies (such as the "bovine arch"). The path of the catheter as reported in the results is highlighted in the area designated 61 in the graphical anatomy display. Also highlighted in the area designated 61 is any missed anatomy in either the report or the coding (engine or human).

As demonstrated in FIG. 4, in one embodiment of the present invention, the interactive, graphical diagram of the vessel anatomy used in the Vascular IR interface translates NLP observations into visual paths representing the path of the catheter. The visual path is set against a gray-scale, static canvas which provides a background of all the vessels, each of which are assigned a label 32 specifying the common name of the vessel. Upon the loading of the coding information for a given note, those vessels which have been identified by the engine or the coder are "activated" in red. To accomplish this, a vessel segment graphic with the red coloration is overlaid on the background at the coordinates in an XML database containing all vessel segment information.

The NLP engine provides a series of line items which correspond to observations in the note. In most cases, the observations are associated with a single vessel or vessel pair (in the case of bilateral). The vessel information is provided using an internal format that identifies the laterality and a terse vessel id (known as the NLP Id). The VasIR interface maps these identifiers to the vessel image file. Additionally, the mapping provides the coordinates of the image segment relative to the canvas. When the diagram is loaded, these images segments are overlaid on the canvas, thus hiding the corresponding gray-scale portion. The mapping also provides the coordinates of the label for the vessel segment so that medical codes (ICD and CPT) relevant to each can be displayed for reference purposes.

Each vessel has one of the following nodes associated with it. The "name" element is the label used on the diagram. The "resourceId" element is the basename of the image file to be placed on the canvas. The "nlpId" is the identifier provided by the NLP engine to represent a vessel observation. The "type" attribute future proofs the database to allow for other vessels types such a veins, stents or grafts. The laterality is one of left, right or blank for unilateral vessels. Finally, the "x", "y", "labelX", "labelY" are the coordinates of the vessel segment and the vessel's CPT code placement relative to the canvas.

In order to provide a rich user experience, the information from this database is loaded into memory and an object representing each node is propagated to the U1 in the form of javascript data structures. It is the javascript that responds to user interactions, placing segments on the canvas, highlighting the selected vessel in gold, and allowing the diagram to be panned while keeping the vessels in place relative to the canvas.

In another embodiment, the present invention uses a database containing anatomical phrases used to described anatomy, the procedure codes they refer to, their relationship to each other (the chains of possible vascular paths), and ties them to the above-described graphical diagram which can be rendered interactively for the human coder as a reference tool.

In yet another embodiment of the present invention, the database and user interface is made available to users through the Internet using HTTP/HTML browser supporting JavaScript and Java. In another embodiment of the present invention, wireless devices, such as cell phones and PDAs can be used to access the system described herein. This allows delivery of the functionality to the users without any installation or locally installed components, facilitating software updates without any action by the user.

A number of embodiments of the present invention have been described. Nevertheless, it will be understood that various modifications may be made without departing from the spirit and scope of the invention. For example, various implementations may change the order in which operations are performed, for instance, the order of the steps in FIG. 1 may be changed. Therefore, depending on the needs and preferences of an implementation, particular operations may be implemented as a combined operation, eliminated, added to, or otherwise rearranged. Accordingly, other embodiments are within the scope of the following claims.

What is claimed:

1. A method comprising:
   receiving, from a remote system via a network connection, a medical report containing natural language;
   extracting, via a computer, at least one language-based feature from the medical report using natural language processing;
   identifying, via the computer, at least one standardized code associated with the extracted at least one language-based feature;
   generating, via the computer, a confidence assessment for the at least one standardized code, wherein the generated confidence assessment indicates the likelihood that the identified standardized code is correct given evidence including the at least one extracted language-based feature;
   generating a medical report-level confidence assessment based on the confidence assessment associated with the at least one standardized code, or if there are more than one confidence assessments, by combining at least two of the more than one confidence assessments;
   selecting, via the computer, one of a plurality of queues based on the medical report-level confidence assessment;
   routing, via the computer, the medical report to the selected queue, and
   receiving, via the network connection, an indication as to whether a human coder approved or modified the medical report;
   wherein the extracting step comprises:
   training, by the computer, a regioning process using a set of training medical reports having pre-annotated sentence elements, wherein each sentence element is a sentence or a phrase;
   assigning, by the computer, a plurality of sentence elements in the medical report into functional regions using the trained regioning process; and
   extracting, by the computer, the at least one language-based feature from one of the functional regions.

2. The method according to claim 1, wherein the processor which computer that extracts the at least one anatomical term language-based feature uses natural language processing.

3. The method of claim 1, wherein the at least one language-based feature comprises at least one anatomical or medical term.

4. The method of claim 1, wherein the at least one standardized code is at least one medical or billing code.

5. The method of claim 1, wherein the generated confidence assessment indicates the probability that the identified standardized code is correct given the evidence including the at least one extracted language-based feature.

6. The method of claim 1, wherein the plurality of queues comprises a confident queue for medical reports that do not require review by a human coder, and at least one review queue for medical reports that require review by a human coder.

7. The method of claim 6, wherein selecting one of a plurality of queues comprises:
comparing the generated medical report-level confidence assessment to a confidence threshold;
selecting the confident queue for receiving the medical report if the generated medical report-level confidence assessment is greater than the confidence threshold; and
selecting the review queue for receiving the medical report if the generated medical report-level confidence assessment is not greater than the confidence threshold.

8. The method of claim 7, wherein the confidence threshold is set manually.

9. The method of claim 1, wherein the medical report-level confidence assessment is the likelihood that a human coder would accept all of the plurality of identified standardized codes as correct without making any changes.

10. The method of claim 1, wherein selectively routing comprises comparing the generated confidence assessment to a confidence threshold.

11. The method of claim 10, wherein the confidence threshold is set manually.

12. The method of claim 1, wherein extracting the at least one language-based feature comprises:
detecting, via the computer, one or more language-based features in the medical report;
matching, via the computer, one or more of the detected language-based features with a standard or variant form of the one or more detected language-based features stored in a database;
normalizing, via the computer, the matched language-based features with the standard form of the language-based features; and
determining, via the computer, one or more insertion points and a directional approach of at least one medical procedure using the normalized language-based features.

13. The method according to claim 12, further comprising determining, via the computer, a sequence and path of vessels using the normalized language-based features based on a database of vessel branching topology.

14. The method according to claim 13, further comprising:
determining, via the computer, one or more physical areas imaged during the medical procedure from one or more of the normalized language-based features; and
determining, via the computer, one or more standardized codes for the medical procedure utilizing one or more of the determined insertion points, the determined directional approach, the determined sequence and path of vessels, and the determined physical areas imaged.

15. The method according to claim 14, wherein determining the one or more standardized codes comprises:
filtering the determined standardized codes based on the determined sequence and path of vessels to remove any standardized codes for a vessel that is on the same path as a more distant vessel having an associated standardized code.

16. The method of claim 1, wherein the at least one identified standardized code is the standardized code that is most probable given the extracted language-based feature.

17. The method of claim 1, wherein generating the confidence assessment is performed independently of extracting the language-based features and identifying the at least one standardized code.

18. The method of claim 1, wherein the confidence assessment is generated using a binary classifier.

19. An apparatus comprising:
a computer configured to:
receive, from a remote system via a network connection, a medical report containing natural language;
training a regioning process using a set of training medical reports having pre-annotated sentence elements, wherein each sentence element is a sentence or a phrase;
assign a plurality of sentence elements in the medical reports into functional regions using the trained regioning process;
extract at least one language-based feature from one of the functional regions using natural language processing;
identify at least one standardized code associated with the extracted at least one language-based feature;
generate a confidence assessment for the at least one standardized code, wherein the confidence assessment indicates the likelihood that the identified standardized code is correct given evidence including the at least one extracted language-based feature;
generate a medical report-level confidence assessment based on the confidence assessment associated with the at least one standardized code, or if there are more than one confidence assessments, by combining at least two of the more than one confidence assessments;
select one of a plurality of queues based on the medical report-level confidence assessment;
route the medical report to the selected queue; and
receive, via the network connection, an indication as to whether a human coder approved or modified the medical report.

20. A method comprising:
(i) receiving, via a second computer over a network connection, sets of one or more standardized codes identified by one or more first computers and, for each identified set of standardized codes, a confidence assessment generated by the first computers for the identified set of standardized codes, wherein each of the first computers identifies a set of standardized codes and generates a confidence assessment by:
(a) receiving a medical report containing natural language;
(b) extracting one or more language-based features from the medical report, wherein the extracting step comprises:
training, by the one or more first computer, a regioning process using a set of medical reports having pre-annotated sentence elements, wherein each sentence element is a sentence or a phrase;
assigning, by the one or more first computers, a plurality of sentence elements in the medical report into functional regions using the trained regioning process; and
extracting, by the one or more first computers, the at least one language-based feature from one of the functional regions;

(c) identifying the set of one or more standardized codes associated with the extracted one or more language-based features; and
(d) generating the confidence assessment for the identified set of standardized codes, wherein the confidence assessment indicates the likelihood that the identified set of one or more standardized codes is correct given evidence including the extracted language-based features;
(ii) receiving, via the second computer, for each of the received identified sets of standardized codes, an indication as to whether a human coder approved or modified the identified set of standardized codes; and
(iii) adjusting, via the second computer, the (d) confidence assessment generating step based on the received indications as to whether a human coder approved or modified the identified set of standardized codes;
(e) select one of a plurality of queues based on the generated confidence assessment; and
(f) route the medical report to the selected queue.

21. The method of claim 20, wherein the first computers generate the confidence assessments using one or more binary classifiers, and wherein adjusting the confidence assessment generating step comprises training the binary classifiers based on the received indications as to whether a human coder approved or modified the identified set of one or more standardized codes.

22. The method of claim 20, wherein modifications to the identified set of standardized codes comprise adding one or more standardized codes to the identified set of standardized codes, deleting one or more standardized codes from the identified set of standardized codes, and/or modifying one or more standardized codes of the identified set of standardized codes.

23. The method of claim 20, wherein the first and second computers comprise different computers.

24. A system comprising:
(i) one or more first computers, each of first computers being configured to identify a set of one or more standardized codes and generate a confidence assessment for the identified set of standardized codes by:
(a) receiving a natural language medical report;
(b) extracting one or more language-based features from the medical report,
wherein the extracting step comprises:
training, by the one or more first computer, a regioning process using a set of medical reports having pre-annotated sentence elements, wherein each sentence element is a sentence or a phrase;
assigning, by the one or more first computers, a plurality of sentence elements in the medical report into functional regions using the trained regioning process; and
extracting, by the one or more first computers, the at least one language-based feature from one of the functional regions;
(c) identifying the set of one or more standardized codes associated with the extracted one or more language-based features; and
(d) generating the confidence assessment for the identified set of standardized codes, wherein the confidence assessment indicates the likelihood that the identified set of one or more standardized codes is correct given evidence including the extracted language-based features;
(ii) a second computer configured to perform a learning process by:
(e) receiving the sets of one or more standardized codes identified by the one or more first computers and, for each identified set of standardized codes, the confidence assessment generated by the one or more first computers for the identified set of standardized codes;
(f) displaying, via a graphical user interface, the identified sets of standardized codes to a human coder;
(g) receiving, for each of the identified sets of standardized codes, an indication as to whether a human coder approved or modified the identified set of standardized codes; and
(h) adjusting the (d) confidence assessment generating step based on the received indications as to whether a human coder approved or modified the identified sets of standardized codes;
(i) select one of a plurality of queues based on the generated confidence assessment; and
(j) route the medical report to the selected queue.

25. The system of claim 24, wherein the one or more first computers are configured to generate the confidence assessments using one or more binary classifiers, and wherein the second computer is configured to adjust the confidence assessment generating step by training the one or more binary classifiers based on the received indications as to whether a human coder approved or modified the identified sets of one or more standardized codes.

26. The system of claim 24, wherein modifications to the identified set of standardized codes comprise adding one or more standardized codes to the identified set of standardized codes, deleting one or more standardized codes from the identified set of standardized codes, and/or modifying one or more standardized codes of the identified set of standardized codes.

27. The system of claim 24, wherein the first and second computers comprise different computers.

* * * * *